CHRYSANTHEMUM PLANT
Filed Oct. 9, 1973 2 Sheets-Sheet 1
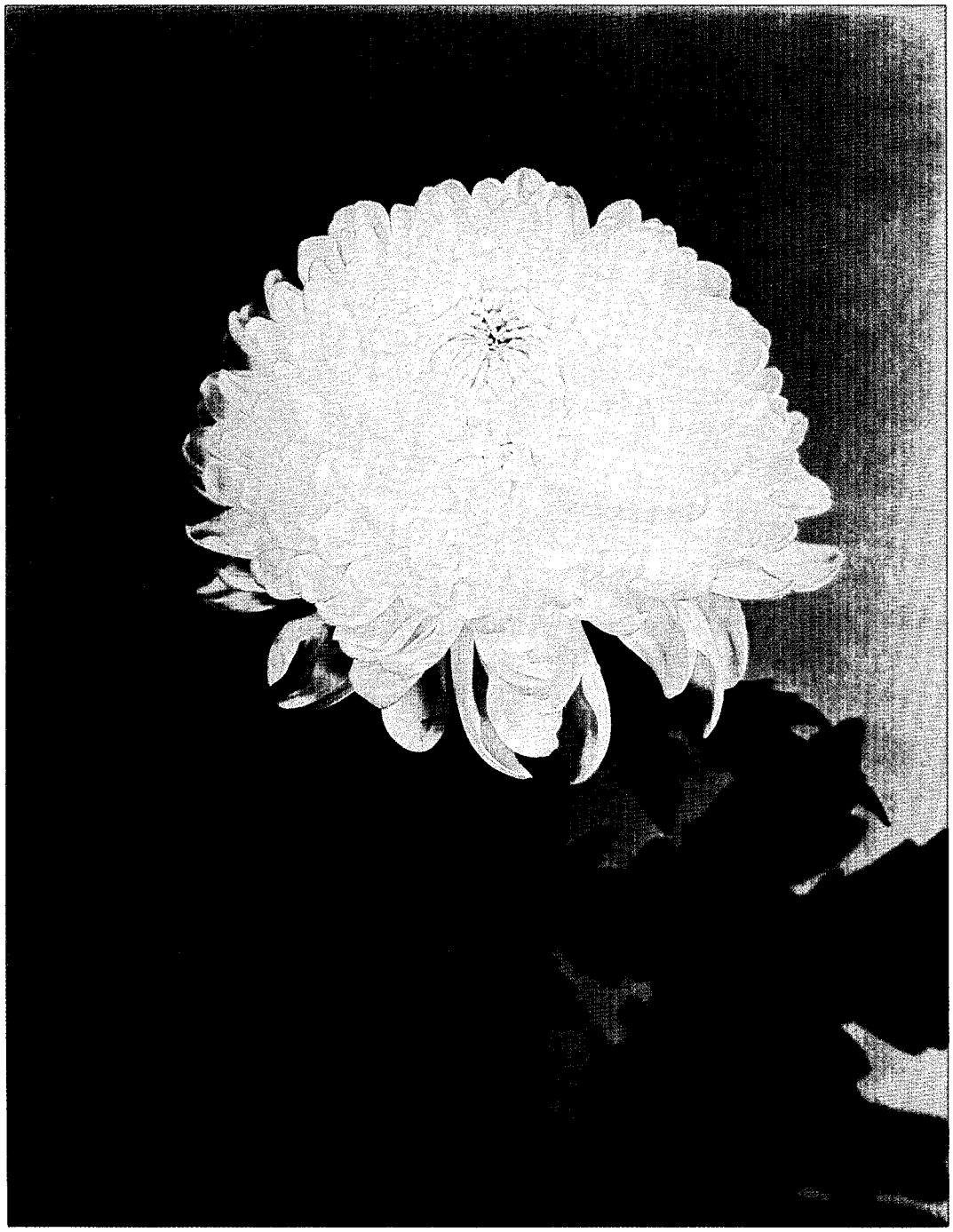

CHRYSANTHEMUM PLANT
Filed Oct. 9, 1973 2 Sheets-Sheet 2
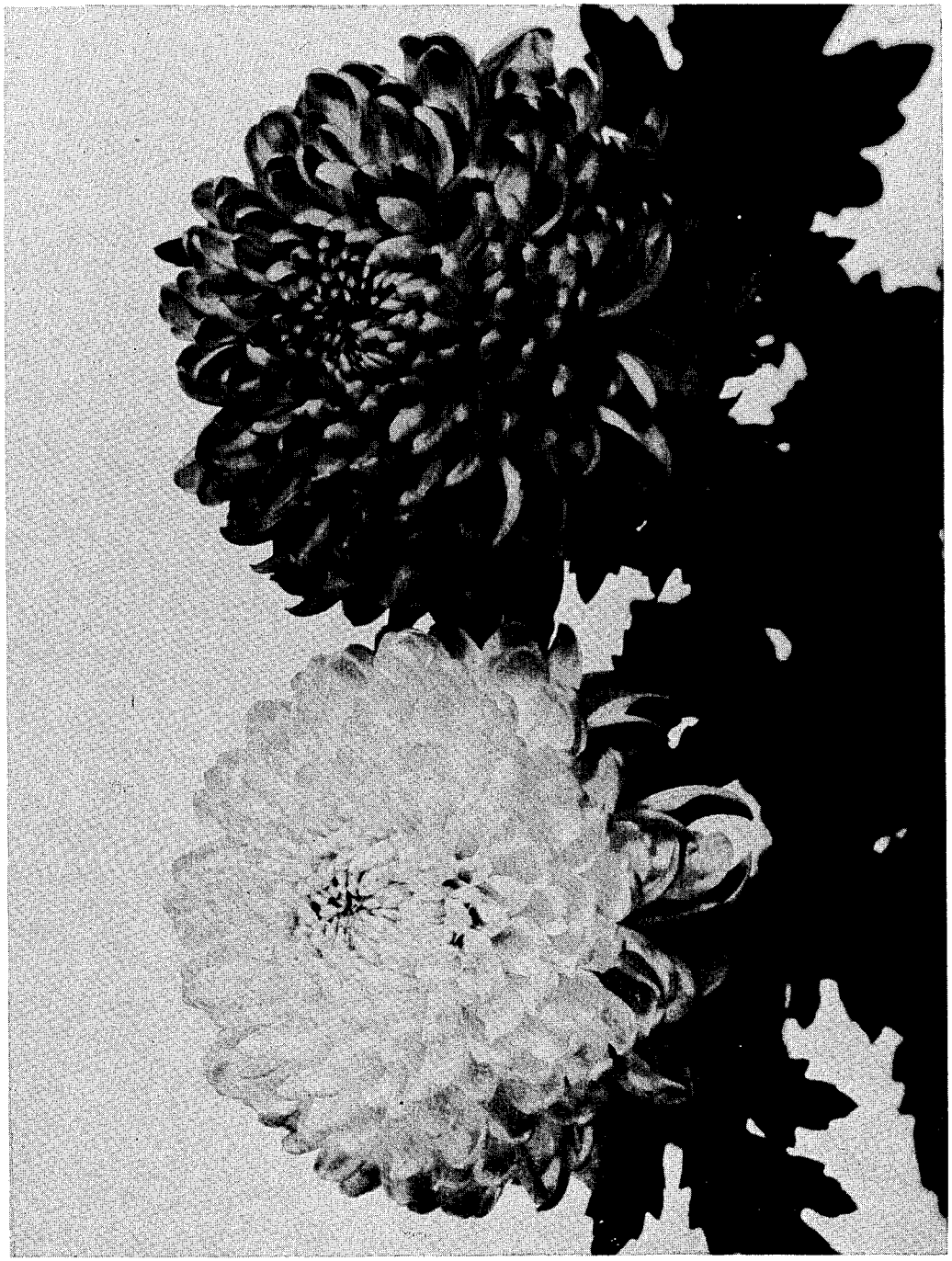

United States Patent Office

Plant Pat. 3,658

Patented Nov. 26, 1974

3,658

CHRYSANTHEMUM PLANT

Walter H. Jessel, Jr., Doylestown, and William E. Duffett, Akron, Ohio, assignors to Yoder Brothers, Inc., Barberton, Ohio Filed Oct. 9, 1973, Ser. No. 404,808
Int. Cl. A01h 5/00
U.S. Cl. Plt.—77 1 Claim The present invention comprises a new and distinct cultivar of chrysanthemum plant known by the varietal name Icecapade, which is a sport of the well-known unpatented cultivar known in the United States as Escapade.

The new cultivar is similar in many respects to Escapade, having the same characteristics of:

1. Equal vigor.
2. Similar durability and shipping qualities.
3. The same recommended period of value as a cut standard.
4. Similar flower form.

The new cultivar is distinguished from Escapade by the following characteristics when grown under comparable conditions:

1. An ivory white flower color when grown at finishing temperatures of 60° F. At temperatures of 58° F. or less some pink tinging will occur.

The new cultivar, when grown in the vicinity of Barberton, Ohio, has a response period of approximately 9 weeks, and the following detailed description is based on observations made of the new cultivar in a greenhouse in Barberton, Ohio. The Response time, blooming period, color, and total vigor may vary significantly with varying environmental conditions such as temperature, daylength, and light intensity.

Suggested flowering in the northern United States is from May through October; southeastern United States, April through November; southwestern United States, April through November; coastal California, March through November, and southern Florida under outdoor conditions, November through April.

In the accompanying photographic drawings, sheet one comprises a color photograph of the new cultivar, and sheet two comprises a black and white comparison photograph of the new cultivar, which appears on the left, and the comparison cultivar Escapade, which appears on the right. The slightly smaller flower size and later response will be noted in the comparison photograph.

In the description which follows, color references are made to the Munsell Color Book, 1963 edition, and comparisons are made with the cultivar Escapade. Where only a single value or description appears for the new cultivar, the same value or description applies to Escapade as well.

Botanical classification: *Chrysanthemum morifolium*

| | Icecapade | Escapade |
|---|---|---|
| Bloom: | | |
| Size | 4½″ | 5″. |
| Fully expanded | 5¼″ | 5¾″. |
| Borne | Singly on disbudded plants | |
| Stems | Strong | |
| Form | Semi-incurve | |
| Permanence | 7-10 days | |
| Color: | | |
| Center of flower | Ivory, 7.5Y9/6 | Lavender, 5RP6/6. |
| Base of petals | Yellow green, 2.5GY7/10 | Greyed lavender, 5RP8/2. |
| Inside of petals | Light yellow 7.5Y9/6 to ivory, 10Y9/1, under finishing temperatures of 60° F. or higher. At finishing temperatures of 58° F. or lower, some pink tinging will occur. | Lavender pink, 10P7/6. |
| Reverse of petals | do | Pale lavender, 10P8/2. |
| Tonality from a distance | Ivory white | Lavender pink. |
| Discoloration | Ivory, 10Y9/1, under finishing temperatures of 60° F. or higher. At finishing temperatures of 58° F. or lower, some pink tinging will occur. | Pale lavender, 10P8/2. |
| Petals: | | |
| Texture | Smooth | |
| Appearance and form | Closed at base, opening slowly to a deep multiridged keel, tapering to a hooded blunt tip. | |
| Arrangement | Composite, whorled on a single receptacle | |
| Persistence | Resist shatter | |
| Fragrance | Typical chrysanthemum | |
| Reproductive Organs: | | |
| Stamen, anthers | None | |
| Pollen | do | |
| Arrangement | Clusters in center of flower, if present | |
| Styles | Present in ray florets | |
| Length | Short | |
| Ovaries | At the base of petal attached to receptacle | |
| Plant: | | |
| Form | Herbaceous | |
| Growth | Upright | |
| Height | Approximately 35″-39″ given 3-4 long day weeks, and a total crop time of 12-13 weeks during recommended period of value as defined in the timetable of Yoder Brothers, Inc., Barberton, Ohio, for the various seasons of the year. | |
| Spread | None, grown single stem to slight grown pinched | |
| Foliage: | | |
| Top side | Medium green, 2.5GY4/4 | Dark green, 10GY2/4. |
| Size | Length to width ratio 17:10 with length to 8½″ and width to 5″ | |
| Quantity | Numerous | |
| Shape | Spatulate lobed | |
| Texture | Smooth | |
| Ribs and veins | Prominent | |
| Edge | Deeply indented | |
| Serration | Slight | |
| Under side | Greyed-green, 7.5GY5/4 | |
| Stipules | Prominent | |

2. Approximately ½″ smaller flower size.
3. Approximately 2–4 days later flowering response.
4. A lighter foliage color.

The new cultivar was selected from a flowering block of the parent cultivar at Barberton, Ohio, and when asexually reproduced by cuttings at Barberton, Ohio, has been found to retain its distinctive characteristics through successive propagations.

We claim:

1. A new and distinct cultivar of chrysanthemum characterized particularly as to its uniqueness when compared to the parent cultivar Escapade by its ivory white flower color at finishing temperatures 60° F. or above; approximately ½″ smaller flower size; approximately 2–4 days later flowering response; and by its lighter foliage color.

No reference cited.

ROBERT E. BAGWILL, Primary Examiner